United States Patent
Vain et al.

(10) Patent No.: US 11,083,664 B2
(45) Date of Patent: Aug. 10, 2021

(54) MECHANOTHERAPEUTIC DEVICE AND MEASUREMENT METHOD

(71) Applicants: UNIVERSITY OF TARTU, Tartu (EE); TARTU HEALTH CARE COLLEGE, Tartu (EE)

(72) Inventors: Arved Vain, Tartu (EE); Reet Linkberg, Tartu (EE); Ivi Vaher, Tartu (EE); Anna-Liisa Parm, Tartu (EE)

(73) Assignee: UNIVERSITY OF TARTU AND TARTU HEALTH CARE COLLEGE, Tartu (EE)

( * ) Notice: Subject to any disclaimer, the term of this patent is extended or adjusted under 35 U.S.C. 154(b) by 579 days.

(21) Appl. No.: 15/123,486

(22) PCT Filed: Mar. 3, 2015

(86) PCT No.: PCT/EP2015/054442
§ 371 (c)(1),
(2) Date: Sep. 2, 2016

(87) PCT Pub. No.: WO2015/132269
PCT Pub. Date: Sep. 11, 2015

(65) Prior Publication Data
US 2017/0071816 A1   Mar. 16, 2017

(30) Foreign Application Priority Data

Mar. 3, 2014 (GB) .................................... 1403692

(51) Int. Cl.
*A61H 7/00* (2006.01)
*A61F 5/01* (2006.01)
(Continued)

(52) U.S. Cl.
CPC ........... *A61H 7/001* (2013.01); *A61F 5/0102* (2013.01); *A61F 5/0104* (2013.01);
(Continued)

(58) Field of Classification Search
CPC .............................. A61H 11/00; A61H 39/04; A61H 2201/1695; A61H 2201/165;
(Continued)

(56) References Cited

U.S. PATENT DOCUMENTS 4,216,547 A   8/1980   Picchione
5,367,708 A   11/1994  Fujimoto
(Continued)

FOREIGN PATENT DOCUMENTS

AU   2011201309 A1   4/2011
EP      1323397 A2   7/2003
(Continued)

OTHER PUBLICATIONS

Gusmao et al., "Angle of Inclination of Femur in Man and its Relationship with Coxa Vara and Coxa Valga", Int. J. Morphol., 29(2), (2011), pp. 389-392 (English Summary).
(Continued)

*Primary Examiner* — Tu A Vo
*Assistant Examiner* — Alexander Morales
(74) *Attorney, Agent, or Firm* — Fay Sharpe LLP (57) ABSTRACT

A device for monitoring a treatment of posture of body parts in which a local mechanotherapeutic stimulus is applied includes an elastic material which is to be worn over the part of the body, a pressure regulating support, a pressure applicator and a pressure sensor. The support is fixed to the elastic material and passes over a region where mechanotherapeutic stimulus is to be applied. The sensor is rigidly attached to the pressure applicator and they are together received in a pocket. The sensor senses pressure and hence a stimulus applied to the part as a result of the tension in the support, the sensor being configured to output a signal indicative of the pressure applied, providing the opportunity to change the
(Continued)

stimulus to within a given range based on the feedback from the sensor. A method for using the device is also disclosed.

17 Claims, 4 Drawing Sheets (51) Int. Cl.
*A61F 5/32* (2006.01)
*A61B 5/00* (2006.01)
(52) U.S. Cl.
CPC .......... *A61F 5/0106* (2013.01); *A61F 5/0123* (2013.01); *A61F 5/32* (2013.01); *A61B 5/6804* (2013.01); *A61B 5/6828* (2013.01); *A61B 2562/0247* (2013.01); *A61F 5/012* (2013.01); *A61H 2201/103* (2013.01); *A61H 2201/165* (2013.01); *A61H 2205/10* (2013.01); *A61H 2205/102* (2013.01)
(58) Field of Classification Search
CPC .... A61H 2201/1654; A61H 2201/1645; A61H 2201/1657; A61H 2201/1664; A61H 2201/1685; A61H 2201/50; A61H 2201/5007; A61H 2201/5058; A61H 2201/5061; A61H 2205/00; A61H 2205/10; A61H 1/006; A61H 1/0237; A61H 2230/085; A61F 5/01; A61F 5/0109; A61F 5/012; A61F 5/32; A61F 5/30; A61F 5/34; A61F 5/0106; A61F 13/061; A61F 13/062; A61F 13/08; A61F 13/085; A61F 2005/0188; A61B 5/00
USPC ...................................... 601/23; 602/5, 9, 23
See application file for complete search history.

(56) References Cited

U.S. PATENT DOCUMENTS

| | | | | |
|---|---|---|---|---|
| 5,795,316 | A * | 8/1998 | Gaylord | A61F 5/0111 |
| | | | | 602/27 |
| 7,730,552 | B2 | 6/2010 | Ota et al. | |
| 10,137,024 | B2 * | 11/2018 | Baym | A61B 5/0031 |
| 2001/0020143 | A1 * | 9/2001 | Stark | A61F 5/012 |
| | | | | 602/13 |
| 2004/0255358 | A1 | 12/2004 | Ota et al. | |
| 2005/0043660 | A1 | 2/2005 | Stark et al. | |
| 2006/0169004 | A1 | 8/2006 | Belluye et al. | |
| 2006/0200057 | A1 | 9/2006 | Sterling | |
| 2008/0195018 | A1 * | 8/2008 | Larson | A61B 17/1325 |
| | | | | 602/53 |
| 2008/0306407 | A1 * | 12/2008 | Taylor | A61B 5/1036 |
| | | | | 600/587 |
| 2009/0320180 | A1 | 12/2009 | Torry | |
| 2010/0042026 | A1 * | 2/2010 | Kloecker | A61F 5/34 |
| | | | | 601/149 |
| 2010/0249686 | A1 * | 9/2010 | Rushton | A61F 5/019 |
| | | | | 602/30 |
| 2011/0000005 | A1 | 1/2011 | Brown | |
| 2011/0041839 | A1 * | 2/2011 | Lee | A61F 5/0193 |
| | | | | 128/96.1 |
| 2011/0160631 | A1 | 6/2011 | Herresthal | |
| 2011/0166635 | A1 * | 7/2011 | Nelson | A61F 7/02 |
| | | | | 607/112 |
| 2012/0165717 | A1 * | 6/2012 | Al Khaburi | A61F 13/08 |
| | | | | 602/75 |
| 2014/0207040 | A1 * | 7/2014 | Ingimundarson | A61F 5/0193 |
| | | | | 602/23 |
| 2014/0303535 | A1 | 10/2014 | Yip et al. | |
| 2014/0323934 | A1 * | 10/2014 | Bertaux-Hegemann | |
| | | | | A61H 9/0078 |
| | | | | 601/148 |
| 2014/0330186 | A1 | 11/2014 | Hyde et al. | |

FOREIGN PATENT DOCUMENTS

| | | |
|---|---|---|
| WO | WO 01/49222 A1 | 7/2001 |
| WO | WO 2006/103422 A1 | 10/2006 |
| WO | WO 2012/089221 | 7/2012 |

OTHER PUBLICATIONS

Janakiramanan et al., "Static Knee Alignment is Associated with the Risk of Unicompartmental Knee Cartilage Defects", Journal of Orthopaedic Research, (Feb. 2008), pp. 225-230.
Kendall et al., "Muscles Testing and Function With Posture and Pain", 5$^{th}$ Edition, (2005), Cover page, introduction page, pp. 50-51, 62-63, 80-83 and 88-89.
Livingston et al., "Optotrak Measurement of the Quadriceps Angle Using Standardized Foot Positions", Journal of Athletic Training, vol. 37, No. 2, Sep. 2002, pp. 252-255.
Stevens et al., "Gait Analysis of Stapling for Genu Valgum", Pediatr Orthop, vol. 24, No. 1, (Jan./Feb. 2004), pp. 70-74.
International Search Report and Written Opinion of International Application No. PCT/EP2015/054442 dated May 28, 2015, 10 pages.
UK Search Report of Application No. GB 1403692.5 dated Sep. 5, 2014, 1 page.

* cited by examiner

MECHANOTHERAPEUTIC DEVICE AND MEASUREMENT METHOD

BACKGROUND

The invention relates to a device for applying a mechanotherapeutic stimulus to a human or animal body and to a method of measuring pressure applied to a human or animal body.

The invention belongs to the field of medical equipment and is intended to be useful in guiding the process of mechanotherapeutic correction of the position of different body parts and to statistically evaluate the effectiveness of correction procedures.

Medicine is developing towards personalized medicine. This process is supported by the rapid development of information technology. New methods and equipment are used which create the opportunity of applying the principles of evidence-based medicine.

In the juvenile ontogenesis stage of a human or an animal there can be changes which are expressed in alterations in the position of the body parts that form joints. As a result, for example, the biomechanical axis may not pass through the centre of the knee or the ankle in lower limbs and this may lead to body weight distributing unevenly on the joint surface which, in turn, may cause arthritis.

A topical medical problem could be, for instance, the development of a child's lower limbs where changes from genu varum to genu valgum and its longitudinal axis of the knee joint is deriving from norm (Gusmao et al 2011). The final angle of the lower limb should stabilize by age six. If the longitudinal axis of the knee joint is not aligned by then but is in genu valgum and this persists even after age seven, physiotherapeutic intervention is called for.

Among such interventions is mechanotherapy. In mechanotransduction, mechanical stimulus changes into electrical and chemical signals in the cells of an organ. This causes changes in the excitability of certain nerve cells, specialized sensory cells and sensory neurons. Stimulating a mechanoreceptor also causes mechanically sensitive ion channels to open and this causes a transduction current that changes the membrane potential of the cell. If the mechanotherapeutic stimulus is dosed optimally, it is possible to stimulate the condition and characteristics of the organ in the desired direction, while simultaneously decreasing the duration of the stimulation process.

In a stable position, the position of the bones in the joints of the legs is determined by the shape of the joint, by the tension of the fascial system, and the tension of the muscles that cross the knee joint (tonus) and, during rotation of a body part (in joints) or movement (regular or during exercise) of a human or animal, by biomechanical and viscoelastic characteristics. For example, if, in relation to the sagittal axis of the knee joint, the sum of the moments of force created by the tonic tension of the muscles that laterally cross the axis is greater than the sum of the moments of force of the medial muscles, it contributes to genu valgum developing: otherwise, genu varum will develop. In case of a balanced position, the sum of the moments of force of antagonistic muscles is zero and the longitudinal axis of the knee joint is aligned with the hip and the ankle on the biomechanical axis.

Genu valgum is expressed in changes in the angle between the longitudinal axis of the tibia and the femur and the shape of the biomechanical axis of the lower limb, tension of the muscles extending across the knee joint and medial collateral ligament, and the compression of lateral joint surfaces. Genu valgum is often associated with tension in the tensor fasciae latae and the iliotibial band even in young children. The tensor fasciae latae, the lateral structures of the knee are shortened; medial knee structures are lengthened. The weakness of the posterior femoral muscles (semimembranosus, semitendinosus and biceps femoris) decreases the medial stability of the knee joint and exacerbates genu valgum; the tendency to laterally rotate from the thigh is increased. Genu valgum is also affected by the weakness of the muscles in the lower limbs and hip region (Kendall et al 2005). Using the myometric method to determine the tone, biomechanical and viscoelastic properties of skeletal muscles (Vain 2012), it is possible to assess the condition of the surface skeletal muscles non-invasively, cost-effectively and in real time.

Genu valgum also affects the knee joint, causing the force that is created while standing or moving to distribute over a significantly smaller joint surface which, in turn, can lead to the onset of arthritis (A.D.A.M. Medical Encyclopaedia).

Treatment is indicated when genu valgum persists beyond age seven. In treating early and mild genu valgum, insoles with arch support which alleviate medial pressure and apply pressure laterally are used in correcting lower limbs. There is a danger of using arch support which is too high; overcorrection can exacerbate genu valgum. Extensive genu valgum is treated with corrective bracing or surgery. Often, the position of the lower limbs can be improved with heat therapy, massage, stretching the muscle or fascia with corrective shoes (Kendall et al 2005).

Genu valgum is accompanied by problems such as the flattening of the longitudinal arch in the foot caused by the unequal distribution of body weight. This, in turn, threatens the musculoskeletal system because the amortisation of the lower limb has decreased. The unequal distribution on the joint surface of the force created while standing or moving can lead to the cartilage wearing down and to the onset of arthritis. The increase of the anterior pelvic tilt increases lumbar lordosis, causes back discomfort, and posture problems. Social problems ensue (low self-esteem) which are caused by being different from other children (Janakiramanan et al 2008; Stevens et al 2004).

One possible effective method of correcting genu valgum could be based on the principle of kinesio tape. Taping is used to correct genu valgum with a lower limb garment, TheraTogs Ultra, developed in the US in 1997. TheraTogs garment is made of a special elastic material GoldTone™ to which is attached tapes of varied width, length, shape and pressure that support and improve postural alignment, improves the conditions of metabolism in the surrounding tissues, and meets the requirements of specific biomechanical training/intervention.

Until now, there has been no equipment or methods to guide and evaluate mechanotherapeutic intervention while the process is on-going so that timely decisions could be made on the effectiveness of the intervention.

Existing patents (AU 2011201309 (A1) Therapeutic brace garment; EP1323397 (A2) Compression stocking for protecting and relieving the knee or ankle joint; U.S. Pat. No. 7,730,552 (B2) Pants garment; US2006169004 (A1) Tights presenting a localized compression effect for practicing a sport; U.S. Pat. No. 4,216,547 (A) Injury protection device for athletes; U.S. Pat. No. 5,367,708 (A) Wearing article for wearing in pressed relation to human body surface; US2009320180 (A1) Garment with enhanced knee support; and US2004255358 (A1) Pants garment), do not offer the possibility of checking the strength of a mechanotherapeutic stimulus or of changing the location of the stimulus while the garment is worn, and the tension of the band is regulated in the garment as a whole, not locally.

WO 2006/103422 A1 discloses a bandage pressure sensor which makes it possible to monitor the pressure of a bandage applied to a region of the human or animal body, for example, to hold a dressing in place or to act as a support.

BRIEF SUMMARY

Viewed from one aspect the invention provides a device for applying a mechanotherapeutic stimulus to a human or animal body, comprising a material which is to be worn over an area of the body, a pressure regulating support having a first portion fixed or removably fixable to the material and a second portion removably fixable to the material to allow for tension in the support to be varied, a sensor for sensing pressure and hence a stimulus applied to the area as a result of the tension in the support, the sensor being configured to output a signal indicative of the pressure applied.

Viewed from another aspect the invention provides a method of measuring pressure applied to a human or animal body, wherein a material is worn over an area of the body, wherein a pressure regulating support has a first portion fixed or removably fixable to the material and a second portion removably fixable to the material to allow for tension in the support to be varied, wherein a sensor is located between the support and the area of the body, and wherein the method comprises:

the sensor sensing pressure applied to the area as a result of the tension in the support; and the sensor outputting a signal indicative of the pressure applied.

By sensing the pressure applied and hence a stimulus applied to the area as a result of the tension in the support, and by the sensor outputting a signal indicative of the pressure applied, it is possible to apply pressure to a chosen site, and to determine the amount of pressure applied locally to the site. The device and method involve both applying pressure and measuring that pressure.

It is possible to use the device and method to estimate the effect of mechanotherapeutic stimulus for several types of condition where muscle tone is causing faulty posture of the body or limb, for example where a biomechanical axis is not correct due to a misbalance in the moment of force in a joint. The device and method may be applicable to various conditions where the longitudinal axes of the body parts are not aligned as they should be. The device and method may be applicable to areas other than joints.

The signal can provide a facility to monitor the pressure applied during mechanotherapy. The signal indicative of the pressure applied may be used to provide information enabling a decision as to whether or not to alter the pressure applied. Alternatively, or additionally, the signal may be used to provide information of the pressure applied over a period of time to enable a medical practitioner to assess historical treatment data.

The pressure applied to the area of the body is preferably a measurable amount of pressure.

The pressure regulating support may be removably fixable to the material at both its first and second portions, for example using hook and loop fastening arrangements. Preferably, the first portion of the support is permanently fixed to the material, for example by a sewn fastening arrangement. The tension in the support can be adjusted between this permanently fixed first portion and the second portion which is removably fixable to the material.

The support may comprise a strap or band or other tension member. Such a tension member may be permanently fixed to the material at one end and loose at the other end, where it may be removably fixable to the material. It may be tightened to increase the pressure applied by pulling in the proximal or the distal direction. For example, if the area of the body to which pressure is to be applied is the knee, then the tension member may be pulled towards the body centre in the proximal direction, or away from the body centre in the distal direction.

The device preferably comprises a garment. The material of the device may then form part of the garment. The material may comprise a suitable fabric, woven or non-woven. The material may be an elastic material, which will facilitate a close fit to the area of the body where pressure is to be applied, and preferably elsewhere too. The garment may be tights, a shirt or a glove for example. The wearing of the garment may be a convenient way of applying pressure to a localized body part to deliver a mechanotherapeutic stimulus. Tights may be useful to provide stimulus to the knee area, for example of a child with genu valgum, or an ankle area. A shirt may be useful to provide stimulus to the back of the shoulder. A glove may be useful to provide stimulus to a finger, for example in therapy for arthritis.

In the case of tights, the first portion of the pressure regulating support may be permanently fixed e.g. sewn to the material of the tights in the waist region, and the second portion may be removably fixable to the material elsewhere. This arrangement would be suitable when the area to which the pressure is to be applied is the knee area. If the area is the ankle area, then the first portion of the support may be permanently fixed e.g. sewn to the material of the tights on the leg thereof i.e. nearer to the ankle, and possibly also in the waist region.

Further in the case of tights, shoulder straps may be provided. The shoulder straps can assist in holding the support. The shoulder straps may be connected to the support, for example by stitching. This may allow for greater tension to be applied to the support and hence the application of a greater pressure to the area of the body. The support may be fixed to the material of the device at a location which is further away from the shoulder straps than the area where pressure is to be applied. By tightening the shoulder straps so as to pull the support the pressure on the area may be increased. For example, it may be the second portion, which is removably fixable to the material, which is at the further away location.

The tension in the support e.g. strap may be sufficient to create the required pressure on the target area of the body. For example where a strap under tension passes over a protuberant body part such as a knee this may generate a local pressure.

The device preferably comprises a pressure applicator for being acted upon by the support to apply pressure to the area of the body. In use, the pressure applicator is located between the support and the area of the body. The pressure applicator may be provided separately of the rest of the device, for location between the support and the target area of the body. This has the benefit of allowing flexibility as to the exact positioning of the pressure applicator. Alternatively, the pressure applicator may be built in to the device.

A preferred embodiment of the device comprises a garment made of fabric, a pressure applicator for applying pressure to a localised part of the body, the support e.g. a strap for holding the pressure applicator in proximity to the body, the support being permanently attached to the fabric of the garment, and the sensor for sensing the pressure applied by the pressure applicator to the localised part.

The device may be adjusted to alter the pressure applied. A decision as to whether to alter the pressure, or to leave it unaltered, may be based on the signal indicative of the pressure applied. It may be determined that the pressure applied is within a desired range, in which case no adjustment is needed. It may be determined that the pressure applied is outside of a desired range, namely too high or too low, in which case adjustment may be made. The signal can therefore provide a means of monitoring the pressure applied and making appropriate adjustment. This makes the device simple to use, as the need for adjustment (or not) can be indicated by the device and the adjustment itself can be made by a wearer or a supervisor of a wearer, and not necessarily by a medical practitioner.

The sensor senses pressure and hence a stimulus applied to the area of the body as a result of the tension in the support, the sensor being configured to output a signal indicative of the pressure applied, providing the opportunity to change the stimulus to within a given range based on the feedback from the sensor.

Pressure may be altered by adjusting the tension of the support e.g. strap. The support may be of the type which sticks to a fabric and can easily be peeled away, tightened or loosened, and then stuck again to the fabric in a new position. A hook and loop fastening arrangement may be used. Such types of fastening arrangement are known for example in adjustable slings.

In preferred embodiments, the sensor is disposed so as to be located between the pressure applicator and the body in use. It can therefore provide an accurate measurement of the pressure applied by the pressure applicator to the localised part of the body. The sensor may be rigidly attached to the pressure applicator. This can assist in giving an accurate measurement of pressure in embodiments having a pressure applicator.

Various types of pressure sensitive sensor may be used. One preferred type comprises a force sensing resistor. These may be in the form of polymer thick film devices that provide a decrease in resistance with increase in force applied to the surface of the sensor.

The pressure applicator preferably comprises a front pressure applying face which in use is proximal to the body, and a rear face which in use is urged by the support towards the body. The pressure applicator may be made of a polymer or silicone or other suitable material. The front face will generally be shaped in a manner suited to the localised part of the body which is to experience the applied pressure, and may in some instances be generally flat. The sensor may be fixed to the pressure applicator e.g. to its front face.

The rear face of the pressure applicator may be generally convex. This works well with a strap or other tension member to convert the tightness of the member into a pressure applied to the localised part of the body. The pressure applicator may be a segment of a sphere, with a part spherical rear face and a flat front face.

The pressure applicator may have a thickness which decreases towards the lateral periphery of the pressure applicator. If a strap or other tension member urges the pressure applicator towards the body, such a shape, with a decrease in thickness towards the lateral periphery, will tend to result in tightening of the strap or other tension member causing the pressure applicator to be urged towards the body with greater force. A pressure applicator with a generally convex rear face and a generally flat front face can achieve this effect.

The device may comprise a pocket for removably receiving the sensor. The pocket can function to hold the sensor in position relative to the support, so that the sensor can sense the pressure applied as a result of the tension in the support. The pocket may be configured to be closable. There may be a closure, such as a closure strap or a hook and loop closure arrangement.

If the device comprises a garment, the pocket can permit the sensor to be removed for washing purposes, for example. The pocket may be provided in the support or in the material. A plurality of pockets may be provided, to allow for the provision of more than one sensor. The pressure applicator may also be received in a pocket. In those embodiments where the sensor is fixed to the pressure applicator, they will be receivable together in a pocket.

The pressure applicator may comprise a plurality of pressure applicator members of different shape and/or size, one or more of said pressure applicator members being selectable to be located between the support and the body. Thus the size, shape and area of the pressure applied to the target area of the body may be adjusted by changing between different pressure applicator members, or combining them together.

The pressure applicator may have its size altered by being inflatable and by varying the amount of fluid e.g. air pumped into the pressure applicator.

The device may be designed to cover a region of the human or animal body, with the pressure applicator being configured to apply pressure to a localised part of said region, whereby pressure at said localised part is greater than that applied by the device to parts of said region adjacent to the localised part. Thus, where the device comprises a garment, for example, the pressure applicator may apply a localised pressure to a particular part of the body, which is greater than the pressure applied to surrounding parts. The device is particularly useful for applying a mechanotherapeutic stimulus to biological tissues.

Preferred methods and devices described herein enable not only the application of pressure through e.g. an elastic band or strap but also the use of additional local pressure on a joint or body part in one or several given points and on an area of desired size.

The device may be configured to apply pressure to the area of the body and also to apply pressure to one or more other areas. Such a second area may be spaced from the first-mentioned area in a distal or a proximal direction. In the case of a joint, e.g. a knee, to which a mechanotherapeutic stimulus is to be applied, a first pressure may be applied to the joint and a second pressure may be applied spaced from the joint. This may be useful in that the second pressure may be applied to a muscle which is responsible for positioning the joint. A third area may also have a pressure applied thereto, which may also be spaced from the joint. For example the pressure may be applied to another muscle responsible for positioning the same joint.

The device may be configured to apply a mechanotherapeutic stimulus to plural areas of the body. It may have a plurality of pressure sensors, so that each area to which pressure is applied can have the pressure there sensed. It may have a plurality of pressure applicators. It may have a plurality of pockets, each for receiving a respective sensor. One support, e.g. strap, may be used to apply a plurality of mechanotherapeutic stimuli each to a respective area of the body, or a plurality of supports, e.g. straps, may be provided each for use to apply a mechanotherapeutic stimulus to at least one area.

The device may comprise a processor for receiving from the sensor the signal indicative of the pressure applied. The processor may be configured to determine whether the pressure applied is within a desired range. The device may then provide a visual or audible indication to a user, or supervisor of the user, as to whether the pressure applied is within a desired range. For example, if the pressure applied is outside of the desired range, then this may be indicated by a light switching on. If the pressure applied falls within the range, then the light may remain off.

A set of indicating lights may be provided for the sensor, or for each sensor in the case of a plurality of sensors. Alternatively, a display (for example a liquid crystal diode display) may show a number indicative of an amount by which the sensed pressure is outside the desired range.

The desired range may be programmed into the device. Thus the target pressure may be predetermined. The desired range may be adjustable by an operator of the device.

The method may comprise calculating from the signal recorded over a period of time an average value representative of the pressure applied over that period of time. The device may have calculating means to perform such a calculation. For example, the device may record the signal, which can also be considered as a measurement, over a five second measurement period at 128 Hz, followed by a five second pause. This gives 640 measurements during the five second measurement period. These 640 measurements are averaged and recorded. Over a longer period, there will be a number of such averaged measurements. For example, over a period of time of one hour there will be 360 of such averaged measurements. Thus the average value representative of the pressure applied for that period of time is obtained.

The method may comprise setting the desired range for a subsequent period of time based on the average value representative of the pressure applied over the first period of time. The device may have range setting means to perform such range setting. The desired range may be set based not just on the average value, but also based on the statistical distribution of the averaged measurements.

The method may comprise evaluating if deviations from the desired range during the second period of time are statistically significant, and indicating to a user if said deviations are statistically significant. The device may have deviation evaluating means to perform such deviation evaluation, and deviation indicating means. The signal indicative of the pressure applied and output by the device may in effect provide an indication of a statistically significant deviation. This can enable a user to adjust the device to reduce or increase the pressure applied, as appropriate.

The processor may record the signal indicative of the pressure applied over a period of time. This allows a medical practitioner effectively to check that an appropriate pressure application, e.g. mechanotherapeutic stimulus, regime has been followed.

The device may be programmed to monitor the pressure applied during mechanotherapy. Such monitoring may be provided in real time.

It is important that the pressure applying effect of the device has minimal fluctuation during the period of application so that it is possible to identify the trends of increase or decrease in the pressure applied, if statistically relevant, as being relevant to changes in mechanotransduction which occur. The existence of feedback that documents and visualises the correction process is an important step towards evidence-based medicine.

The device may be provided with a suitable power supply, such as a battery. It may comprise a data interface enabling it to download data from an external resource, such as a computer, or to upload data to such a resource. The data interface may be a wireless system, or the device may have a USB socket, for example. If data relating to the sensed pressure is uploaded in real time, then a medical practitioner may be able to evaluate the stimulus applied.

Data relating to the sensed pressure is preferably retrievably recorded by the device.

In other aspects, the invention provides a method and a device for monitoring a treatment of posture of different body parts in which a local mechanotherapeutic stimulus is applied to a subject, e.g. a human or animal subject.

Viewed from another aspect the invention provides a method for monitoring a treatment in which a mechanotherapeutic stimulus is applied to a subject (e.g. a human or animal), comprising applying pressure to a part of the body of a subject, so as to provide a mechanotherapeutic stimulus to that part, sensing the pressure applied to the part, and outputting from the sensor a signal indicative of the pressure applied.

Thus, when providing a mechanotherapeutic treatment, for example the treatment of faulty posture, information can be provided to a medical practitioner about the pressure applied. The practitioner can decide based on the information how to proceed with the treatment. This information may be used to adjust the pressure applied, and/or to assess after a treatment period data relating to the pressure applied over that period. The ability for a practitioner to monitor the pressure applied in mechanotherapeutic treatment is not known in existing treatments.

Such a method may be useful in a method of treating genu valgum as well as other joints, unilaterally or bilaterally. It may also be used to treat different deformations in the left or right sides of the body. In case of genu valgum, the tibiofemoral angle of the lower limb and changes in the biomechanical axis are registered with the goniometric method (Livingston, L. A., Spaulding, S. J. 2002); the changes that occurred in the skeletal muscles that cross the knee joint with the myometric method (Vain 2012). If the assessments from these methods are within the normal range and the position of the limb has normalised, the mechanotherapeutic procedure may be stopped.

The method preferably comprises recording the signal indicative of the pressure applied over a period of time. With this arrangement, data may be provided over a period of pressure application. The results may be viewed e.g. on a computer and changes that occurred during the monitoring period, for example due to a biological response to a mechanotherapeutic stimulus delivered by the pressure application, may be assessed by a medical practitioner.

BRIEF DESCRIPTION OF THE DRAWINGS

Certain preferred embodiments of the invention will now be described, by way of example only, with reference to the accompanying drawings, in which.

DETAILED DESCRIPTION

Figure 1:
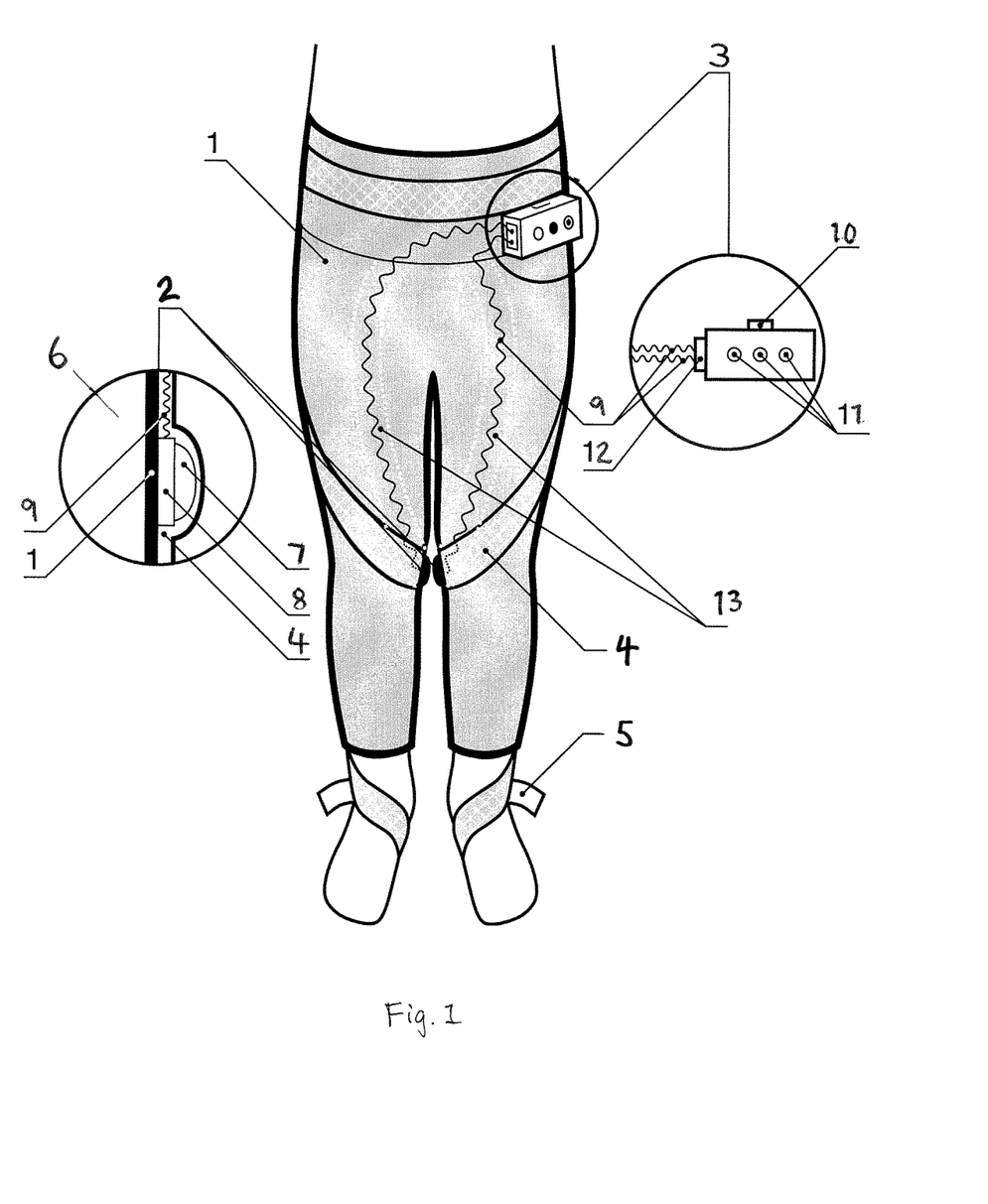
FIG. 1 is a front view of the device being worn by a subject.
Figure 2:
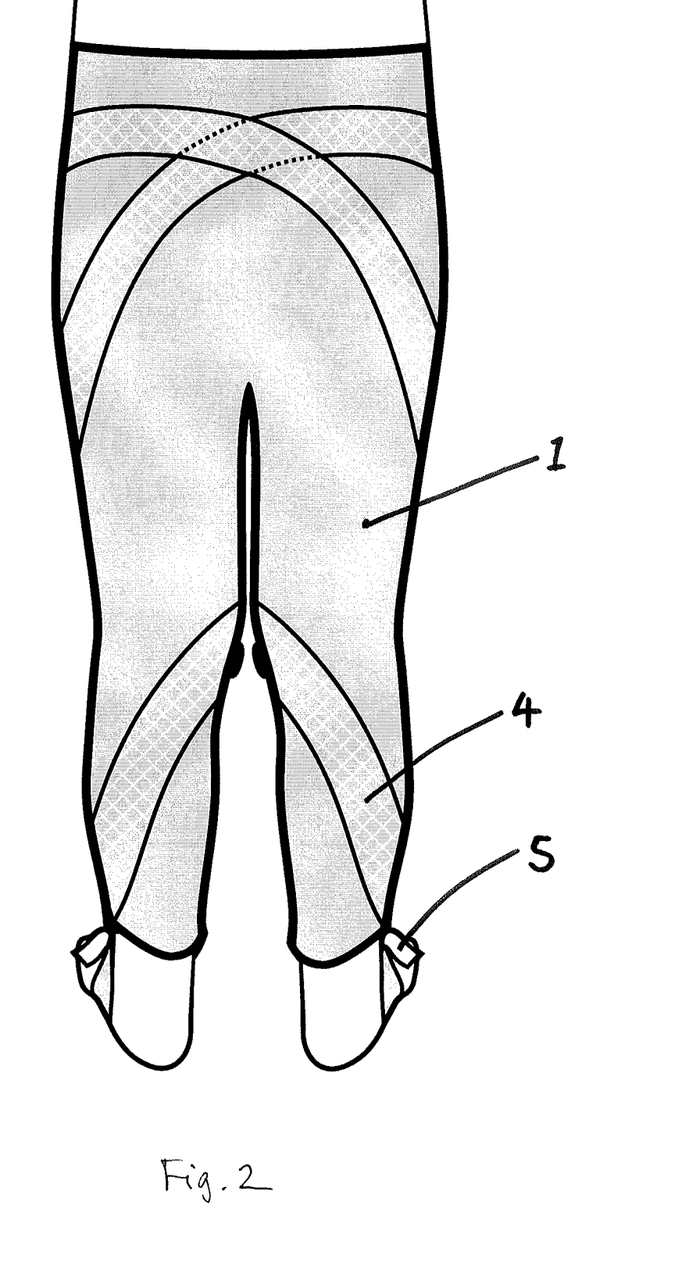
FIG. 2 is a rear view of the device as worn by the subject.

Referring to the embodiment of FIGS. 1 and 2, a device for applying pressure to a human or animal body comprises a garment 1 made of elastic material, a pressure applying mechanism 2 and a control unit 3.

The garment 1 is provided with two straps 4 of elastic material sewn to the material of the garment. The garment is in the form of tights and the straps are sewn to the tights in the waist region. Thus the straps are permanently fixed to the material of the garment. The straps 4 are otherwise initially loose and may be placed over or run along the regions where mechanotherapeutic stimulus is needed. In this embodiment each strap is wound around a respective leg 6 of the wearer. The straps 4 are capable of being applied to the garment material with a tension as determined by a supervisor of a wearer, or by the wearer. The straps 4 are removably attachable at regions 5 thereof to themselves or to the garment material, for example by using known hook and loop fastening means.

Two pressure applying mechanisms 2 are shown in this embodiment. Each pressure applying mechanism is received in a pocket at a location where it is desired to apply, and monitor, the pressure, or the mechanotherapeutic stimulus. Additional pockets may be provided elsewhere on the garment in alternative embodiments requiring the mechanotherapeutic stimulus to be applied to other parts of the body of the subject.

The pressure applying mechanism comprises a pressure applicator including a pressure applicator member in the form of a spherical segment 7. The pressure applicator member is removably received in the pocket so that different pressure applicator members may be used to vary the "footprint" of the pressure applied or the amount of pressure applied.

The pressure applying mechanism 2 further comprises a pressure sensor 8, which may for example be a force sensing resistor. The pressure sensor 8 is rigidly attached to the spherical segment 7. A suitable sensor is the FSR 402 "Round force sensing resistor" available from Interlink Electronics. In this embodiment the force sensing resistor has a diameter of about 13 mm and a thickness of about 0.5 mm.

The pressure sensor 8 is located between the pressure applicator member 7 and the material of the garment 1. Adjustment of the pressure applied to the localised part of the body of the subject can be effected by adjusting the tightness of the strap 4 which passes over the outside of the pressure applicator mechanism. Because the pressure applicator member has a part-spherical rear face the tightness of the strap is effectively converted into forward pressure towards the body. The sensor senses the amount of this pressure. For a given strap tightness the pressure may also be altered by changing the pressure applicator member. A thicker member may produce a greater localised pressure for a given strap tightness compared to a thinner member. The pressure applicator member has a front face, proximal to the body of the wearer, which may have a desired shape and size to effect the desired mechanotherapeutic stimulus. A smaller face area will produce a higher pressure for a given force caused by the strap. A larger face area will spread the force over a larger area, and hence will produce a lower pressure. Therefore, by using different pressure applicator members, different shapes of the area of applied pressure may be achieved, as well as different applied pressures. In some embodiments more than one pressure applicator member may be received in a pocket, to give the effect of a thicker pressure applicator overall.

The sensor 8 is connected by wires 9 to the control unit 3. The wires extend along channels 13 in the garment. By being contained in the channels, the wires cannot be easily tampered with. The channels may be created by strips of material sewn to the material of the tights.

The control unit 3 comprises a printed circuit board, a power supply in the form of a battery, a USB socket, a microchip, a real time clock, and a user interface. The control unit is appropriately programmed with software. The user interface includes an on-off switch 10, light or sound indicators 11, and sockets 12 for receiving the wires 9. In other embodiments, there may be wireless communication between the sensor 8 and the control unit 3.

Figure 3:
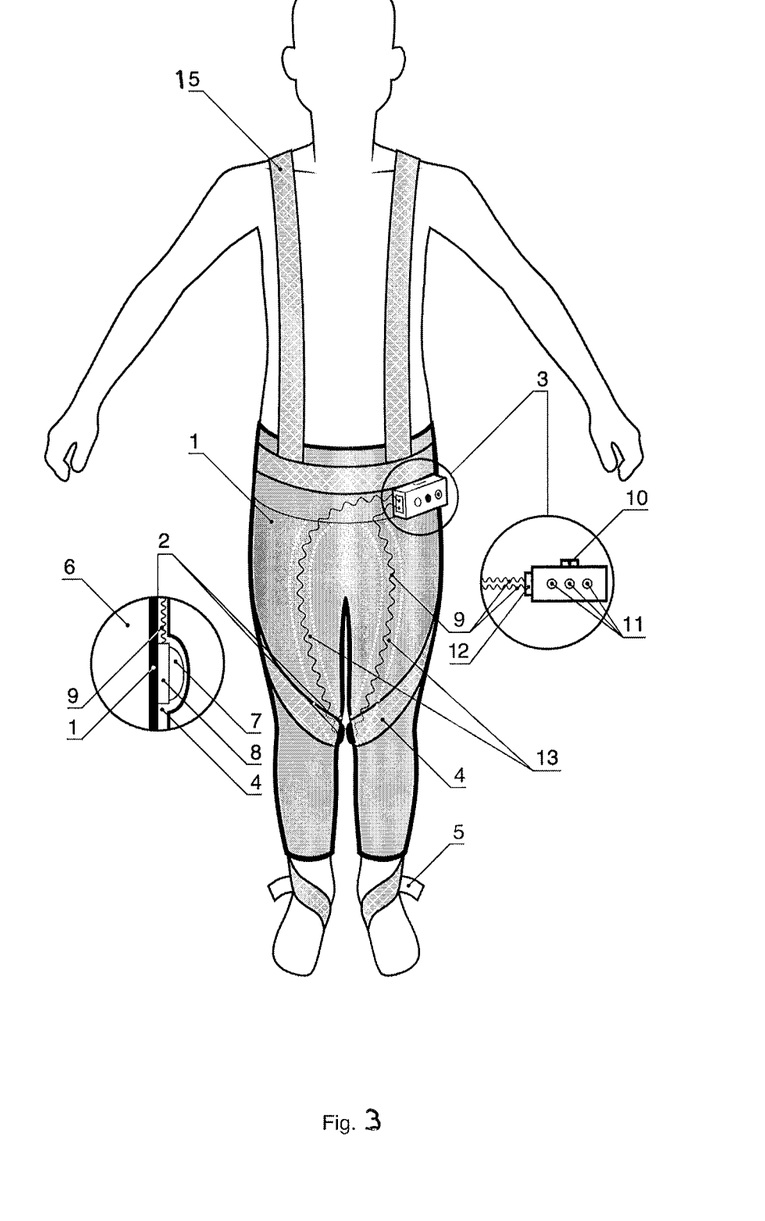
FIG. 3 is a front view of a modified device being worn by a subject.
Figure 4:
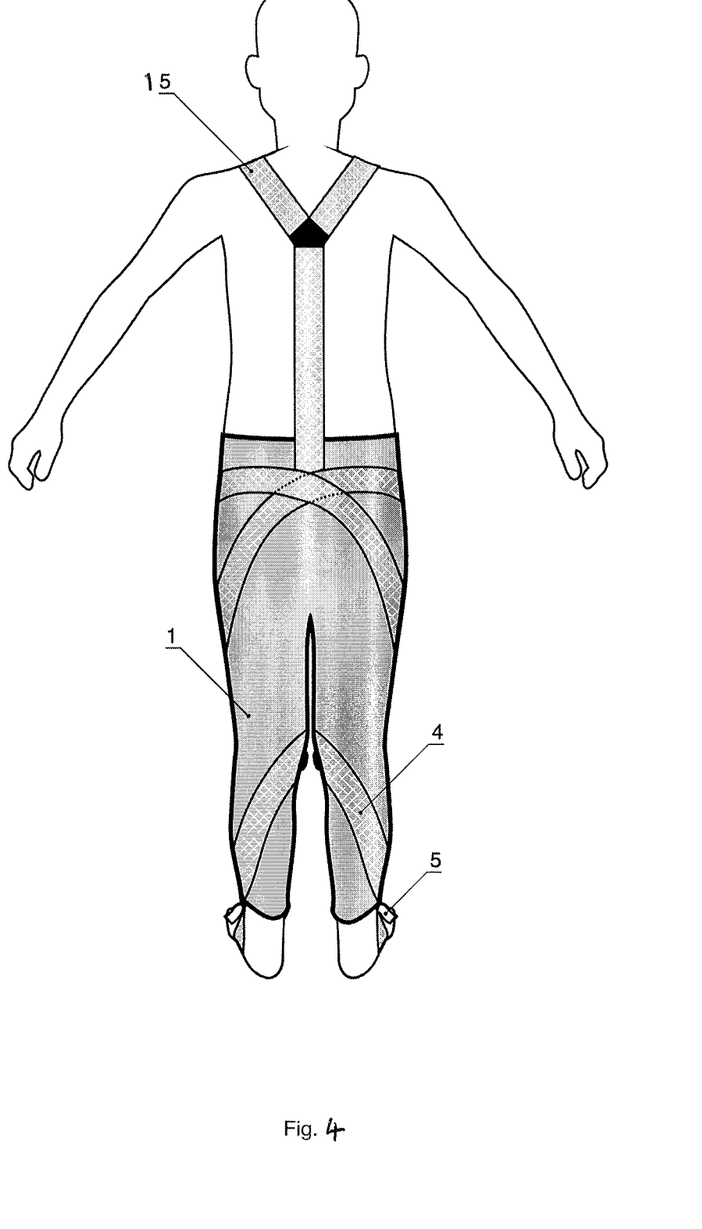
FIG. 4 is a rear view of the modified device as worn by the subject.

The embodiment of FIGS. 3 and 4 is similar to that of FIGS. 1 and 2, and like parts are shown with corresponding reference numerals. The description of the like parts will not therefore be repeated. The embodiment of FIGS. 3 and 4 differs from that of FIGS. 1 and 2 in that shoulder straps 15 are provided, connected to the straps 4, and passing over the subject's shoulders. The shoulder straps can assist in holding the straps in position. This may allow for greater tension to be applied to the straps and hence the application of a greater pressure to the area or areas of the body where mechanotherapeutic stimulus is needed.

In use of either of the above described embodiments, the device applies pressure to a human or animal body to create a mechanotherapeutic stimulus at a localised part of the body. The stimulus has the desired parameters, in terms of location, size of the area over which the pressure is applied, and amount of pressure. The device allows an operator of the device, who may be a wearer or a supervisor, to know if the stimulus is within the desired parameters and to adjust the device if necessary. It also allows continuous evaluation of the stimulus in real time or at predetermined intervals. After a period of the device having been worn by a subject, the operator can review the pressure applied over that time period.

The device is activated with switch 10 which turns on the sensor 8 and the control unit for receiving a signal from the sensor 8 indicative of the pressure applied. If the pressure placed on the localised part of the body by the pressure applicator member 7 is within a desired range that ensures that the aims of the stimulus are met, one of the signal lights 11 on the control unit 3 is turned off. Otherwise, the light is turned on, signalling that the pressure is below or above the desired range. This may also be accompanied by a sound signal, or a sound signal may be used instead of a light signal. In any event, the signal indicates to an operator if adjustment is required, and if so, whether the pressure should be increased or decreased.

Pressure may be increased or decreased by adjusting the tension in the strap 4. The strap 4 is removably attachable at region 5 thereof to itself or to the garment material, and so can be removed to allow tension in the support to be increased or decreased and then reattached. In the case of the embodiment of FIGS. 3 and 4, there is an additional option of adjusting the shoulder straps 15 to increase or decrease the amount of their pulling on the strap 4, thereby increasing or decreasing the pressure. This works well if the region 5 of the strap 4 is at the time of shoulder strap adjustment attached to itself or to the garment material.

The software programmed into the control unit records the signal from the sensor at predetermined intervals and over a desired period. After the observation period ends, the control unit may be connected via the USB socket to a computer and suitable software on the computer visualises the results of the mechanotherapeutic stimulus applied over the observation period. The software may include the capability of providing statistical evaluation of any changes that occurred during the observation period.

The method and the device can help genu valgum as well as other joints both unilaterally and bilaterally, as well as different deformations in the left and right sides of the body.

This specification discloses a method of how to monitor, measure, assess, record and give feedback to the operator about an ongoing stimulus process. The device can encompass the whole limb without fixing it or limiting its natural movement, which is extremely important for any developing muscle (in children for example). It is possible to choose one or more points to be locally stimulated and monitored and the area to be stimulated can vary in size. The amount of pressure allocated can be changed in controlled manner depending on the condition and individual needs of the subject, which can be entered into the device program by a medical person and can vary from sensor to sensor if needed. The operator (parent or supervisor or the person wearing the device e.g. garment, i.e. a non-medical person) can operate the device between visits to a doctor or other medical practitioner. The practitioner may then obtain recorded data from the device during the subject's visit to see how the measurements have changed, and then change the settings of the device to specify a higher or lower target pressure. For example the practitioner may wish to achieve a gradual step-by-step change. The use of the device may be discontinued if the required effect such as a balance in muscle tone, or if a reference value of the muscle tone, has been reached.

The device described in relation to the drawings relates to applying pressure at the knee. The invention is not limited to a device used in this manner or a corresponding method. The device may be used to estimate the effect of mechanotherapeutic stimulus for several types of condition where muscle tone is causing faulty posture of the body or limb e.g. where a biomechanical axis is not correct due to misbalance in moment of force in a joint. In other words, the device may be used in any situation where longitudinal axes of the body parts are not aligned as they should be.

For example, when a person has different tone in muscles crossing the ankle, the sole of the foot would touch the ground in a manner causing the heel of footwear to wear excessively. The actual problem is that the joint will erode and cause faulty posture and accompanying problems to the person. An embodiment of the device may be used to stimulate the muscles crossing the ankle in a controlled manner. The amount of optimal pressure may be determined for the subject by a doctor and entered into the program of the device, depending on the condition of the subject. There may be one or more stimulus points, and each may have a different desired pressure value. The device and method can provide the possibility to control the whole stimulation process.

In the preferred embodiment a pressure applying mechanism having at least one pressure applicator member is used. However, the desired pressure may in some circumstances be achieved by using the pressure regulating support without a pressure applicator member.

There are however advantages to the use of a pressure applicator member. For example, when a garment is initially worn the pressure regulating support may provide sufficient pressure in the desired region, without being too tight elsewhere. However as it may loosen with use, it may not be possible to tighten it without causing discomfort or restricting the wearer's movement. At that point a pressure applicator member may be added to add more pressure at a specific location, thereby avoiding the negative effects of the support being too tight.

The invention claimed is:

1. A device for applying a mechanotherapeutic stimulus to a human or animal body, comprising tights configured to be worn over a lower portion of the body, the tights comprising a material which is to be worn over a knee of the body, an elastic pressure regulating tension member having a first portion fixed to a waist portion of the tights and a second portion which in use is fixable to and removable from a bottom portion of the tights to allow for tension in the tension member to be varied, a pressure applicator for being acted upon by the tension member to apply pressure to said knee of the body, the tension member and pressure applicator configured to be placed over the knee of the body, the pressure applicator comprising a front pressure applying face which in use is proximal to the body, and a rear face, a sensor for sensing pressure and hence a stimulus applied to the knee as a result of the tension in the tension member, the sensor being configured to output a signal indicative of the pressure applied, wherein the rear face of the pressure applicator is generally convex and in use is urged by the tension member towards the body, and wherein the pressure applicator comprises a plurality of pressure actuator members, the plurality of pressure actuator members being configured to actuate, more than one of said pressure actuator members of the plurality of pressure actuator members being selectable to be located between the tension member and said knee of the body such that at least one of an amount, shape and area of the pressure applied to the said knee of the body is adjusted by one of:
   removing a pressure actuator member of the plurality of pressure actuator members;
   removing a pressure actuator member of the plurality of pressure actuator members and replacing the removed pressure actuator member with at least one other pressure actuator member of the plurality of pressure actuator members; and combining together pressure actuator members of the plurality of pressure actuator members.

2. A device as claimed in claim 1, wherein the sensor is disposed so as to be located between the pressure applicator and the body in use.

3. A device as claimed in claim 1, wherein the pressure applicator has a thickness which decreases towards a lateral periphery of the pressure applicator.

4. A device as claimed in claim 1, wherein a thickness of the pressure applicator is variable.

5. A device as claimed in claim 1, wherein at least one of the plurality of pressure actuator members differs from another of said pressure actuator members in respect to at least one of its shape and size.

6. A device as claimed in claim 1, wherein the tension member comprises a strap.

7. A device as claimed in claim 1, comprising a pocket for removably receiving the sensor, the pocket including a closure.

8. A device as claimed in claim 1, comprising a processor for receiving from the sensor the signal indicative of the pressure applied.

9. A device as claimed in claim 8, wherein the processor is configured to determine whether the pressure applied is within a desired range, and wherein the processor is configured to provide at least one of a visual and an audible indication as to whether the pressure applied is within the desired range.

10. A device as claimed in claim 1, wherein the pressure applicator is inflatable.

11. A method of measuring pressure applied to a human or animal body, wherein tights are configured to be worn over a lower portion of the body, the tights comprising a material that is worn over a knee of the body, wherein an elastic pressure regulating tension member has a first portion fixed to a waist portion of the tights and a second portion which in use is fixable to and removable from a bottom portion of the tights to allow for tension in the tension member to be varied, wherein a pressure sensitive sensor capable of outputting a signal indicative of a sensed pressure is located between the tension member and the knee of the body, wherein a pressure applicator is located between the tension member and the knee of the body, the tension member and pressure applicator configured to be placed over the knee of the body, the pressure applicator comprising a front pressure applying face which in use is proximal to the body, and a rear face, wherein the rear face of the pressure applicator is generally convex and in use is urged by the tension member towards the knee of the body, and wherein the pressure applicator comprises a plurality of pressure actuator members, the plurality of pressure actuator members being configured to actuate, more than one of said pressure actuator members of the plurality of pressure actuator members being selectable to be located between the tension member and said knee of the body such that at least one of an amount, shape and area of the pressure applied to the said knee of the body is adjusted by one of:

removing a pressure actuator member of the plurality of pressure actuator members;

removing a pressure actuator member of the plurality of pressure actuator members and replacing the removed pressure actuator member with at least one other pressure actuator member of the plurality of pressure actuator members; and combining together pressure applicator members of the plurality of pressure actuator members, and wherein the method comprises:

the tension member urging the rear face of the pressure applicator towards the knee of the body as a result of tension in the tension member, said tension being determined by the fixing of the second portion of the tension member to the material;

the pressure applicator applying pressure to the knee of the body as a result of said urging;

the sensor sensing said pressure applied to the knee of the body; and the sensor outputting a signal indicative of the pressure applied.

12. A method as claimed in claim 11, comprising determining from the signal indicative of the pressure applied if the pressure applied is within a desired range.

13. A method as claimed in claim 12, comprising determining the desired range for an individual subject.

14. A method as claimed in claim 12, comprising calculating from the signal recorded over a period of time an average value representative of the pressure applied over that period of time.

15. A method as claimed in claim 14, comprising setting the desired range for a subsequent period of time based on the average value.

16. A method as claimed in claim 15, comprising evaluating if deviations from the desired range during the subsequent period of time are statistically significant, and indicating to a user if said deviations are statistically significant.

17. A method as claimed in claim 11, comprising recording the signal indicative of the pressure applied.

* * * * *